(12) United States Patent
Yang et al.

(10) Patent No.: US 10,538,484 B1
(45) Date of Patent: *Jan. 21, 2020

(54) MALEAMIC ACID MONOMER AND PREPARATION METHOD AND USE THEREOF

(71) Applicants: China Petroleum & Chemical Corporation, Beijing (CN); SINOPEC Research Institute of Petroleum Engineering, Beijing (CN)

(72) Inventors: Xiaohua Yang, Beijing (CN); Yongxue Lin, Beijing (CN); Jian He, Beijing (CN); Lin Wang, Beijing (CN); Haibo Wang, Beijing (CN); Fan Yang, Beijing (CN); Zhoujun Li, Beijing (CN); Xiaoqiang Dong, Beijing (CN)

(73) Assignees: China Petroleum & Chemical Corporation, Beijing (CN); SINOPEC Research Institute of Petroleum Engineering, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/129,285

(22) Filed: Sep. 12, 2018

(51) Int. Cl.
*C07C 235/28* (2006.01)
*C07H 5/04* (2006.01)
(Continued)

(52) U.S. Cl.
CPC .......... *C07C 235/28* (2013.01); *C07C 231/02* (2013.01); *C07H 5/04* (2013.01);
(Continued)

(58) Field of Classification Search
None
See application file for complete search history.

(56) References Cited

U.S. PATENT DOCUMENTS 5,204,366 A * 4/1993 Lavanish ............... A01N 37/46
514/424
5,369,198 A * 11/1994 Albrecht ............ C04B 24/2658
526/240

(Continued)

FOREIGN PATENT DOCUMENTS

CN 107033280 A 8/2017
JP 2000007628 * 1/2000
(Continued)

OTHER PUBLICATIONS

Werbin ("Cyclization of N-Succinylglycine Dimethyl Ester" J. Am. Chem. Soc. 1947, vol. 69, p. 1681-1684) (Year: 1947).*

*Primary Examiner* — Amy C Bonaparte
(74) *Attorney, Agent, or Firm* — Novick, Kim & Lee, PLLC; Allen Xue

(57) ABSTRACT

A maleamic acid monomer, and a preparation method and a use of the maleamic acid monomer. The structural formula of the monomer is as follows:

(Continued)

formula (1), wherein, R is selected from

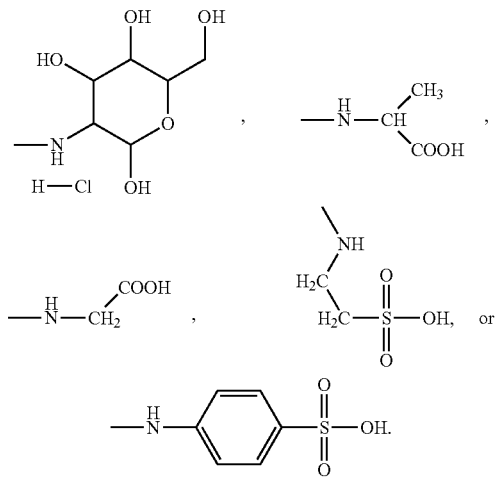

The maleamic acid monomer provided in the present invention may be used as a comonomer to prepare temperature-tolerant and calcium salt-tolerant polymers.

6 Claims, 2 Drawing Sheets

(51) Int. Cl.
  *C07C 231/02* (2006.01)
  *C07C 309/21* (2006.01)
  *C07C 309/29* (2006.01)
  *C07C 235/30* (2006.01)

(52) U.S. Cl.
  CPC .......... *C07C 235/30* (2013.01); *C07C 309/21* (2013.01); *C07C 309/29* (2013.01)

(56) References Cited

U.S. PATENT DOCUMENTS

2012/0138300 A1  6/2012  Bray et al.
2017/0107418 A1  4/2017  Zhou et al.
2019/0092997 A1*  3/2019  Lin .......................... C09K 8/24

FOREIGN PATENT DOCUMENTS

WO  2015042026 A1  3/2015
WO  2015047261 A1  4/2015
WO  2017120496 A1  7/2017

* cited by examiner

Wave Number / cm⁻¹

δ /ppm

MALEAMIC ACID MONOMER AND PREPARATION METHOD AND USE THEREOF

FIELD OF THE INVENTION

The present invention relates to the field of synthesis of maleamic acid compounds, in particular to a maleamic acid monomer, and a preparation method and a use of the maleamic acid monomer.

BACKGROUND OF THE INVENTION

Maleamic acid compounds are a sort of important organic substances, and maleimide compounds prepared from such organic substances serving as intermediates through a catalyzed ring-closure reaction are widely studied in biological chemistry, organic chemistry, and polymer chemistry. Maleamic acids can become functional monomers in themselves through molecular design and can be used to prepare high-performance water-soluble polymers through self-polymerization or copolymerization, because they have asymmetric carbon atoms, amide structure, carboxyl group, and a variety of designable N-substituent groups.

Maleamic acid compounds are usually synthesized from maleic anhydride and amino-bearing compounds through an acylation reaction. However, synthetic maleamic acids studied and produced at present are in a small variety and have poor water solubility, and their preparation processes have demanding requirements for reaction temperature and apparatus, and involve complex steps. Therefore, the preparation processes can't meet the demand for simple preparation of a number of water-soluble chemical agents.

Besides, in industrial sectors such as petroleum engineering, waste water treatment, paper making, and textile, etc., the demand for polymer additives becomes higher and higher. That means it is highly necessary to design and synthesize monomer molecules that have special constructions.

SUMMARY OF THE INVENTION

To meet the requirements of temperature-tolerant and calcium salt-tolerant polymer additives for polymers in special constructions, the present invention provides a maleamic acid monomer, a preparation method and a use of the maleamic acid monomer. The synthesis of the monomer happens under mild conditions, and is safe, easy and simple to manipulate, and the monomer may be used as an ideal raw material for synthesizing temperature-tolerant and calcium salt-tolerant random copolymers.

To attain the objects described above, in a first aspect, the present invention provides a maleamic acid monomer, which is represented by the following structural formula:

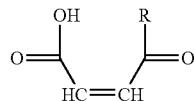

formula (1), wherein, R is selected from

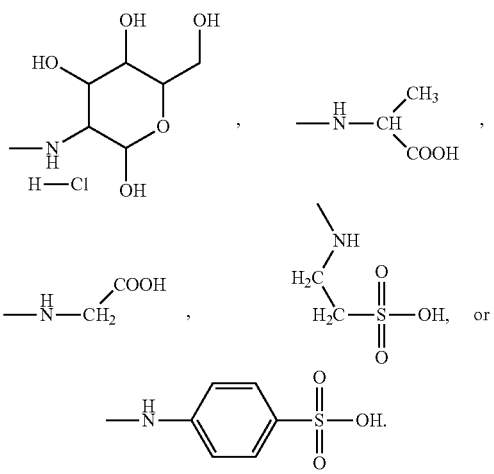

Preferably, R is selected from

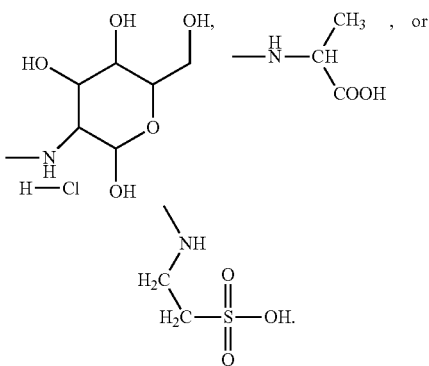

Preferably, the maleamic acid monomer is selected from N-glucose hydrochloride maleamic acid represented by structural formula

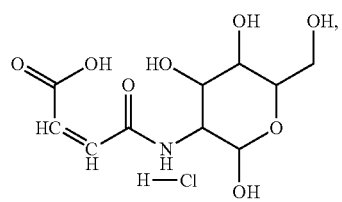

N-isopropionyloxy maleamic acid represented by structural formula

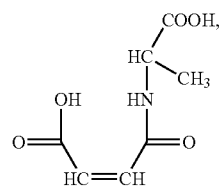

or N-ethylsulfonyl maleamic acid represented by structural formula

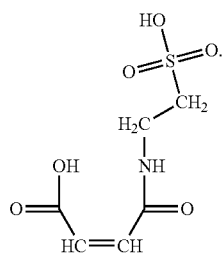 [SMILES: O=C(O)/C=C\C(=O)NCCS(=O)(=O)O]

In a second aspect, the present invention provides a method for preparing the maleamic acid monomer described in the present invention, which comprises:

(1) Dissolving C mol amino-compound in B1 mL solvent;
(2) Mixing A mol maleic anhydride with B2 mL solvent; then adding the solution obtained in the step (1) by dropwise adding while stirring;
(3) Stirring the product obtained in the step (2) for reaction, till white precipitate is generated and the white precipitate doesn't increase anymore;
(4) Filtering the reaction product obtained in the step (3) by suction filtration, and washing and drying the obtained product, so that the maleamic acid monomer is obtained;

the amino-compound is selected from glucosamine hydrochloride, α-alanine, aminoacetic acid, taurine acid, or aminobenzenesulfonic acid.

Preferably, the amino-compound is selected from glucosamine hydrochloride, α-alanine, or taurine acid.

Preferably, A:(B1+B2):C=(1-1.4):(40-120): 1.

Preferably, the solvent is tetrahydrofuran, glacial acetic acid, propionic acid, or dimethyl formamide.

Preferably, in the step (3), the reaction temperature is 25-50° C., and the reaction time is 1-6 h.

In a third aspect, the present invention provides a use of the maleamic acid monomer provided in the present invention in preparation of temperature-tolerant and calcium salt-tolerant polymers. With the technical scheme described above, the maleamic acid monomer provided in the present invention may be used as a comonomer to prepare temperature-tolerant and calcium salt-tolerant polymers.

DETAILED DESCRIPTION OF THE EMBODIMENTS

Figure 1:
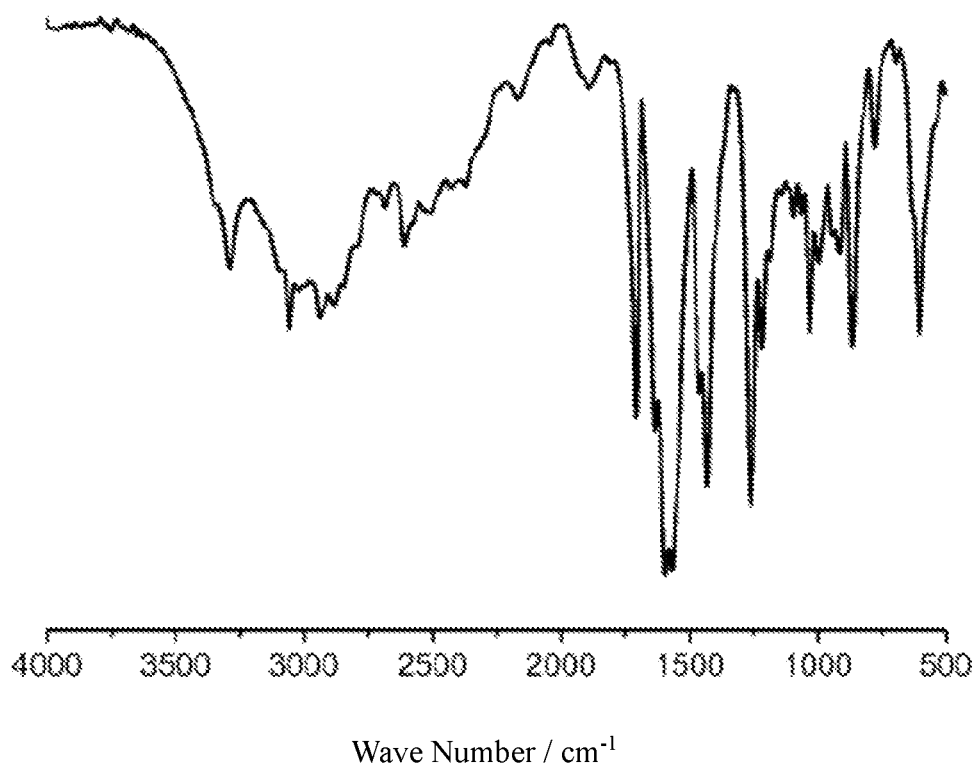
FIG. 1 is an infrared absorption spectrogram of the N-glucose hydrochloride maleamic acid prepared in examples 1-5.

The ends points and any value in the ranges disclosed in the present invention are not limited to the exact ranges or values; instead, those ranges or values shall be comprehended as encompassing values that are close to those ranges or values. For numeric ranges, the end points of the ranges, the end points of the ranges and the discrete point values, and the discrete point values may be combined to obtain one or more new numeric ranges, which shall be deemed as having been disclosed specifically in this document.

In a first aspect, the present invention provides a maleamic acid monomer, which is represented by the following structural formula:

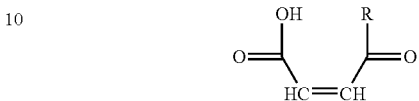

formula (1), wherein, R is selected from

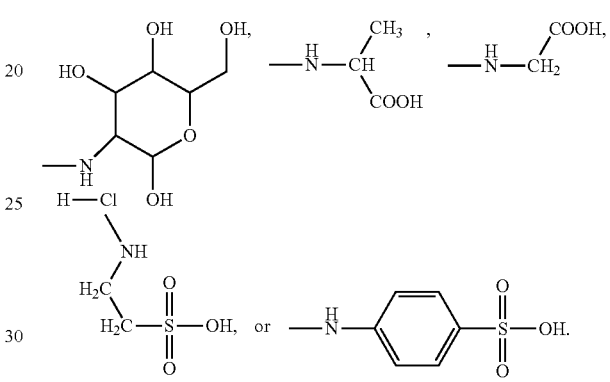

According to the present invention, preferably, R is selected from

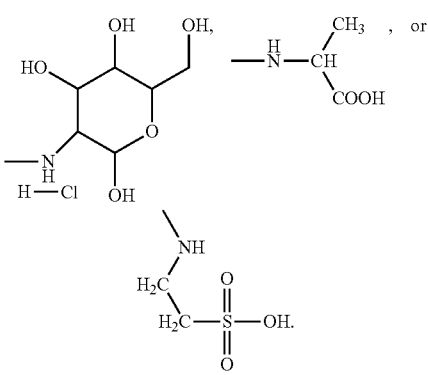

According to the present invention, preferably, the maleamic acid monomer is selected from N-glucose hydrochloride maleamic acid represented by structural formula

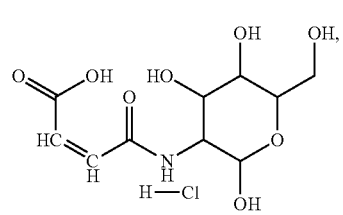

N-isopropionyloxy maleamic acid represented by structural formula

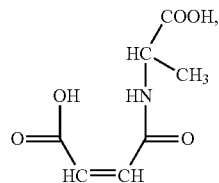

or N-ethylsulfonyl maleamic acid represented by structural formula

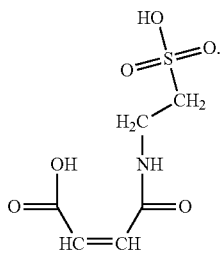 [SMILES: O=C(O)/C=C\C(=O)NCCS(=O)(=O)O]

The maleamic acid monomer described above in the present invention can have an amidation reaction according to the raw materials that participate in the synthesis, so that the ring in the maleic anhydride is opened, and the structure can be ascertained by infrared absorption spectroscopy and $^1$H-NMR spectroscopy.

In a second aspect, the present invention provides a method for preparing the maleamic acid monomer described in the present invention, which comprises:

(1) Dissolving C mol amino-compound in B1 mL solvent;

(2) Mixing A mol maleic anhydride with B2 mL solvent; then adding the solution obtained in the step (1) by dropwise adding while stirring;

(3) Stirring the product obtained in the step (2) for reaction, till white precipitate is generated and the white precipitate doesn't increase anymore;

(4) Filtering the reaction product obtained in the step (3) by suction filtration, and washing and drying the obtained product, so that the maleamic acid monomer is obtained;

the amino-compound is selected from glucosamine hydrochloride, α-alanine, aminoacetic acid, taurine acid, or aminobenzenesulfonic acid.

For example, when the preparation method provided in the present invention is used to prepare N-glucose hydrochloride maleamic acid, an amidation reaction is executed according to the following reaction equation, so that the ring in the maleic anhydride is opened:

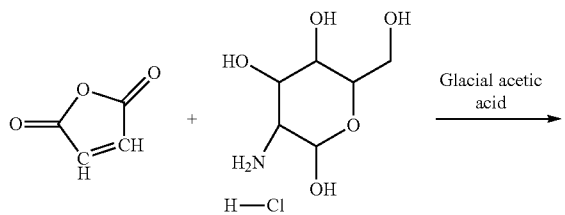

-continued

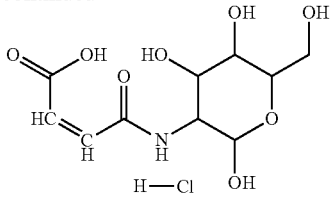

According to the present invention, the maleic anhydride and the amino-compound are raw materials for reaction in the preparation method. Preferably, the amino-compound is selected from glucosamine hydrochloride, α-alanine, or taurine acid. The maleamic acid monomer prepared from the amino-compound may be an ideal monomer for preparing temperature-tolerant and calcium salt-tolerant polymers.

According to the present invention, in the steps (1) and (2), the raw material, maleic anhydride and amino-compound may be dissolved in a solvent respectively to form reaction solutions first, before the reaction and synthesis is executed. Preferably, the solvent is tetrahydrofuran, glacial acetic acid, propionic acid, or dimethyl formamide.

According to the present invention, the raw material for reaction, maleic anhydride and amino-compound may be at a certain quantitative relation; preferably, A:(B1+B2):C=(1-1.4):(40-120):1. At the quantitative relation, the yield of the prepared maleamic acid monomer is higher. Wherein, C mol amino-compound is fully dissolved in B1 mL solvent. A mol maleic anhydride may be fully dissolved in B2 mL solvent. The dose ratio of B1 to B2 may be about 1:1.

According to the present invention, in the reaction of the raw material, maleic anhydride and amino-compound in step (3), the extent of the reaction may be judged on the basis of the occurrence of white precipitate. Preferably, in the step (3), the reaction temperature is 25-50° C., and the reaction time is 1-6 h.

In the present invention, the step (4) is used to make post-treatment of the obtained reaction product to remove the solvent and obtain the product of synthesis. Both the suction filtration and the washing may conventional operations in the art. The drying may be vacuum-drying (at reduced pressure) at 40-60° C. for 10-16 h. White powder is obtained after drying. The obtained white powder is ascertained as the maleamic acid monomer provided in the present invention according to the amidation reaction in which the ring in maleic anhydride is opened, as analyzed by infrared absorption spectroscopy and $^1$H-NMR spectroscopy. Measured according to the raw material input in the preparation method and the quantity of the obtained product, the yield ratio of the prepared maleamic acid monomer is 70% or higher.

In the present invention, by introducing the structure of the amino-compound (especially the structure of glucosamine hydrochloride) into the monomer structure, the water solubility of the monomer can be improved, and the tolerance of the monomer to micromolecular electrolytes and high temperature can be improved, and the monomer becomes an ideal monomer for preparing temperature-tolerant and calcium salt-tolerant polymeric materials.

In a third aspect, the present invention provides a use of the maleamic acid monomer provided in the present invention in preparation of temperature-tolerant and calcium salt-tolerant polymers. The maleamic acid monomer provided in the present invention, especially the N-glucose hydrochloride maleamic acid, may be used as a monomer to have a copolymerization reaction with acrylamides or acrylic monomers to prepare temperature-tolerant and calcium salt-tolerant filtrate reducers for drilling fluids.

Compared with the prior art, the maleamic acid monomer provided in the present invention is a novel amino-compound, which not only can be used as an intermediate for imide chemicals, but also can be directly used as a raw material or functional monomer for aqueous phase reactions. The method employed in the present invention has advantages including simple and safe reaction conditions, easy operation, and high yield.

Hereunder the present invention will be detailed in embodiments.

Example 1

1.4 mol maleic anhydride is loaded into a dry three-neck round flask, 40 mL glacial acetic acid is poured into the flask to dissolve the maleic anhydride, additional 40 mL glacial acetic acid solution in which 1.0 mol glucosamine hydrochloride is dissolved is added slowly by drop-wise adding into the flask while the mixture is stirred, then the mixture is stirred for 3 h at 25° C. for reaction, and the generated white precipitate is filtered by suction filtration, and washed and dried.

Figure 2:
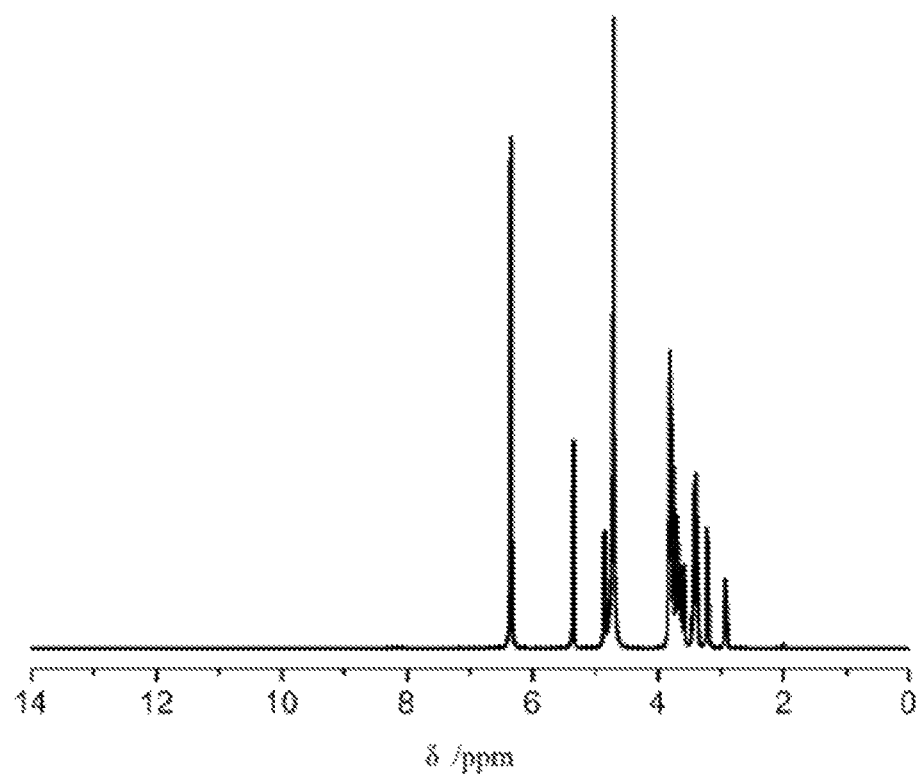
FIG. 2 is a $^1$H-NMR spectrogram of the N-glucose hydrochloride maleamic acid prepared in examples 1-5.

The obtained product is analyzed by infrared spectroscopy and $^1$H-NMR spectroscopy, as shown in FIGS. 1 and 2. Wherein, attribution analysis is carried out for the H in the $CH_2$ group, CH group, and double bonds in the $^1$H-NMR spectrogram: $\delta(\times 10^{-6})$: 6.18 ($H_a$, 1); 6.88 ($H_b$, 1); 2.93 ($H_c$, 1); 4.51 ($H_d$, 1); 3.73 ($H_e$, 1); 3.43 ($H_f$, 1); 3.41 ($H_g$, 2); 5.90 ($H_h$, 1). According to the amidation reaction of the raw material and the analysis of the infrared spectrogram and $^1$H-NMR spectrogram, the product is N-glucose hydrochloride maleamic acid represented by a structural formula

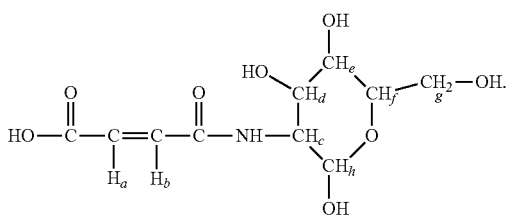

After weighing and calculation, the yield ratio of the product is 77%. The melting point of the product is 171° C.

Example 2

1.2 mol maleic anhydride is loaded into a dry three-neck round flask, 25 mL glacial acetic acid is poured into the flask to dissolve the maleic anhydride, additional 15 mL glacial acetic acid solution in which 1.0 mol glucosamine hydrochloride is dissolved is added slowly by drop-wise adding into the flask while the mixture is stirred, then the mixture is stirred for 2 h at 50° C. for reaction, and the generated white precipitate is filtered by suction filtration, and washed and dried.

Analyzed by infrared spectroscopy and $^1$H-NMR spectroscopy, the result is the same as that in the example 1, i.e., the obtained product is N-glucose hydrochloride maleamic acid.

After weighing and calculation, the yield ratio is 72%. The melting point of the product is 169° C.

Example 3

1.2 mol maleic anhydride is loaded into a dry three-neck round flask, 60 mL glacial acetic acid is poured into the flask to dissolve the maleic anhydride, additional 60 mL glacial acetic acid solution in which 1.0 mol glucosamine hydrochloride is dissolved is added slowly by drop-wise adding into the flask while the mixture is stirred, then the mixture is stirred for 6 h at 30° C. for reaction, and the generated white precipitate is filtered by suction filtration, and washed and dried.

Analyzed by infrared spectroscopy and $^1$H-NMR spectroscopy, the result is the same as that in the example 1, i.e., the obtained product is N-glucose hydrochloride maleamic acid. After weighing and calculation, the yield ratio is 70%. The melting point of the product is 171° C.

Example 4

1.1 mol maleic anhydride is loaded into a dry three-neck round flask, 40 mL propionic acid is poured into the flask to dissolve the maleic anhydride, additional 40 mL propionic acid solution in which 1.0 mol glucosamine hydrochloride is dissolved is added slowly by drop-wise adding into the flask while the mixture is stirred, then the mixture is stirred for 3 h at 35° C. for reaction, and the generated white precipitate is filtered by suction filtration, and washed and dried. Analyzed by infrared spectroscopy and $^1$H-NMR spectroscopy, the result is the same as that in the example 1, i.e., the obtained product is N-glucose hydrochloride maleamic acid.

After weighing and calculation, the yield ratio is 75%. The melting point of the product is 172° C.

Example 5

1.0 mol maleic anhydride is loaded into a dry three-neck round flask, 40 mL tetrahydrofuran is poured into the flask to dissolve the maleic anhydride, additional 40 mL tetrahydrofuran solution in which 1.0 mol glucosamine hydrochloride is dissolved is added slowly by drop-wise adding into the flask while the mixture is stirred, then the mixture is stirred for 4 h at 20° C. for reaction, and the generated white precipitate is filtered by suction filtration, and washed and dried. Analyzed by infrared spectroscopy and $^1$H-NMR spectroscopy, the result is the same as that in the example 1, i.e., the obtained product is N-glucose hydrochloride maleamic acid.

After weighing and calculation, the yield ratio is 73%. The melting point of the product is 170° C.

Example 6

1.2 mol maleic anhydride is loaded into a dry three-neck round flask, 50 mL glacial acetic acid is poured into the flask to dissolve the maleic anhydride fully, additional 40 mL glacial acetic acid solution in which 1.0 mol α-alanine is dissolved is added slowly by drop-wise adding into the flask while the mixture is stirred, then the mixture is stirred at a low stirring rate for 3 h at 30° C. for reaction; thus, white precipitate is generated gradually. After the reaction is completed, the product is filtered by suction filtration, washed, filtered again by suction filtration, and then vacuum-dried.

Figure 3:
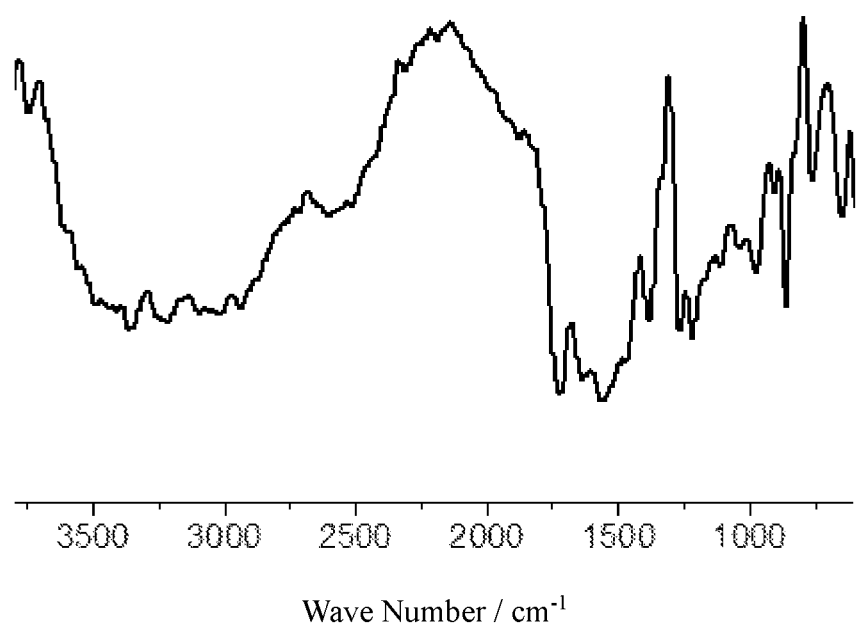
FIG. 3 is an infrared absorption spectrogram of the N-isopropionyloxy maleamic acid prepared in example 6.

The obtained product is analyzed by infrared spectroscopy and $^1$H-NMR spectroscopy, the obtained infrared spectrogram is shown in FIG. 3, and attribution analysis is carried out for the H in the $CH_3$ group, CH group and double bonds in the $^1$H-NMR spectrogram: $\delta(\times 10^{-6})$: 6.51 ($H_a$, 1); 6.73 ($H_b$, 1); 3.91 ($H_c$, 1); 1.48 ($H_d$, 3). According to the amidation reaction of the raw material and the analysis of the infrared spectrogram and $^1$H-NMR spectrogram, the product is N-isopropionyloxy maleamic acid represented by a structural formula

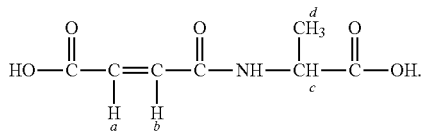

After weighing and calculation, the yield ratio of the product is 80%.

Example 7

1.1 mol maleic anhydride is loaded into a dry three-neck round flask, 50 mL glacial acetic acid is added into the flask to dissolve the maleic anhydride fully, and additional 35 ml glacial acetic acid solution in which 1.0 mol taurine acid is dissolved is added into the flask slowly while the mixture is stirred. The mixture is stirred at 35° C. for 3 h for reaction, so that white precipitate is generated gradually. After the reaction is completed, the product is filtered by suction filtration, washed, filtered again by suction filtration, and then vacuum-dried.

The obtained product is analyzed by infrared spectroscopy and $^1$H-NMR spectroscopy, and attribution analysis is carried out for the H in the $CH_2$ group and double bonds in the obtained $^1$H-NMR spectrogram: $\delta(\times 10^{-6})$: 6.47 ($H_a$, 1); 6.78 ($H_b$, 1); 2.70 ($H_c$, 2); 3.05 ($H_d$, 2). According to the amidation reaction of the raw material and the analysis of the infrared spectrogram and $^1$H-NMR spectrogram, the product is N-ethylsulfonyl maleamic acid represented by a structural formula

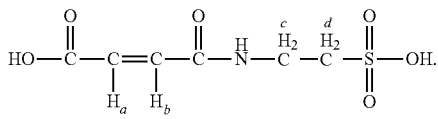

After weighing and calculation, the yield ratio of the product is 70%.

Example 8

15 pbw acrylamide, 15 pbw 2-acrylamido-2-methyl propanesulfonic acid, and 10 pbw N-glucose hydrochloride maleamic acid prepared in the example 1 are copolymerized by free radical polymerization in water solution, and the obtained copolymer is used as a polymeric filtrate reducer for drilling fluids.

API filter loss measurement is carried out for the polymeric filtrate reducer.

The API filter loss is 220 mL after raw mud-1 (high-salinity compound brine mud) is aged at 150° C. for 16 h.

The API filter loss is 20 mL or less after the raw mud-1 is added with 1.5 wt % above-mentioned polymeric filtrate reducer and is aged at 150° C. for 6 h.

The API filter loss is 190 mL after raw mud-2 (brine mud that contains 8 wt % calcium chloride) is aged at 150° C. for 16 h.

The API filter loss is 30 mL or less after the raw mud-2 is added with 1.5 wt % above-mentioned polymeric filtrate reducer and is aged at 150° C. for 16 h.

The results indicate that the synthetic polymeric filtrate reducer has good temperature-tolerant and calcium salt-tolerant performance.

While the present invention is described above in detail in some preferred embodiments, the present invention is not limited to those embodiments. Various simple variations, including combinations of the technical features in any other appropriate way, can be made to the technical scheme of the present invention within the scope of the technical concept of the present invention, but such variations and combinations shall be deemed as disclosed content in the present invention and falling in the protection scope of the present invention.

The invention claimed is:

1. A maleamic acid monomer having formula (1):

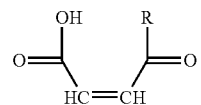

formula (1), wherein R is

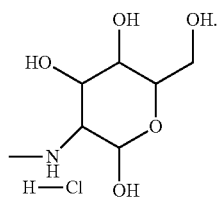

2. A method for preparing the maleamic acid monomer according to claim 1, comprising:
   (1) dissolving an amino-compound in a solvent to form a first solution;
   (2) mixing maleic anhydride with the solvent to form a second solution; then adding the first solution obtained in the step (1) dropwise into the second solution while stirring;
   (3) stirring the mixture obtained in the step (2) to form a white precipitate in the mixture; and
   (4) suction filtering, washing, and drying the white precipitate to obtain the maleamic acid monomer,
   wherein the amino-compound is glucosamine hydrochloride.

3. The method according to claim 2, wherein the first solution comprises C moles of the amino-compound and B1 mL of the solvent wherein the second solution comprises A moles of maleic anhydride and B2 mL of the solvent, and wherein A:(B1+B2):C=(1-1.4):(40-120):1.

4. The method according to claim 2, wherein the solvent is tetrahydrofuran, glacial acetic acid, propionic acid, or dimethyl formamide.

5. The method according to claim 2, wherein the step (3) is carried out at a reaction temperature of 25-50° C., and a reaction time of 1-6 h.

6. A method for preparing a temperature-tolerant and calcium salt-tolerant polymer, comprising: copolymerizing the maleamic acid monomer of claim 1 with arylamides or acrylic monomers.

* * * * *